United States Patent
Zhang et al.

(10) Patent No.: US 8,779,199 B2
(45) Date of Patent: Jul. 15, 2014

(54) AGOMELATINE INTERMEDIATES AND PREPARATION METHOD THEREOF

(75) Inventors: Peng Zhang, Shanghai (CN); Yu Huang, Shanghai (CN); Zhedong Yuan, Shanghai (CN); Hanbin Shan, Jiangxi province (CN); Xiong Yu, Shanghai (CN)

(73) Assignee: Les Laboratoires Servier, Suresnes Cedex (FR)

( * ) Notice: Subject to any disclaimer, the term of this patent is extended or adjusted under 35 U.S.C. 154(b) by 74 days.

(21) Appl. No.: 13/702,388

(22) PCT Filed: Jun. 8, 2011

(86) PCT No.: PCT/CN2011/075438
§ 371 (c)(1),
(2), (4) Date: Jun. 3, 2013

(87) PCT Pub. No.: WO2011/153939
PCT Pub. Date: Dec. 15, 2011

(65) Prior Publication Data
US 2013/0267738 A1    Oct. 10, 2013

(30) Foreign Application Priority Data
Jun. 8, 2010 (CN) .......................... 2010 1 0197370

(51) Int. Cl.
C07C 233/22 (2006.01)
C07C 231/06 (2006.01)
C07C 233/18 (2006.01)
C07C 231/12 (2006.01)

(52) U.S. Cl.
CPC ............. C07C 231/06 (2013.01); C07C 233/18 (2013.01); C07C 2102/10 (2013.01); C07C 233/22 (2013.01); C07C 231/12 (2013.01)
USPC ............................ 564/219; 564/124; 564/126

(58) Field of Classification Search
CPC .. C07C 231/06; C07C 231/065; C07C 233/22
USPC .......................................... 564/124, 126, 219
See application file for complete search history.

(56) References Cited

U.S. PATENT DOCUMENTS

| | | | |
|---|---|---|---|
| 7,981,923 B2 * | 7/2011 | Harris et al. ................... | 514/424 |
| 2005/0182258 A1 | 8/2005 | Schmidhammer et al. | |
| 2009/0131719 A1 | 5/2009 | Souvie et al. | |

FOREIGN PATENT DOCUMENTS

| | | |
|---|---|---|
| CN | 1680296 A | 10/2005 |
| CN | 1293048 C | 1/2007 |
| CN | 101486665 A | 7/2009 |

OTHER PUBLICATIONS

Written Opinion for PCT/CN2011/075438 of Aug. 23, 2011.
Chu, G. et al., "Synthesis of naphthalenic melatonin receptor ligand" Synthetic Communication, vol. 31, No. 4, p. 621-629, 2001.
International Search Report for PCT/CN2011/075438 of Jul. 5, 2011.

* cited by examiner

*Primary Examiner* — Shailendra Kumar
(74) *Attorney, Agent, or Firm* — Hueschen and Sage

(57) ABSTRACT

The present invention relates to the intermediate compounds for preparation of agomelatine, as well as the preparation methods thereof The intermediate of the present invention for preparation of agomelatine is compound A as shown in the following formula. Also provided are two novel intermediate compounds. When we use these new intermediate compounds to prepare agomelatine, it is simple to manipulate, well-controlled and with high purity, without complicated operations such as rectification and column chromatography separation, and suitable for industrial production. Meanwhile, the preparation methods of the two new intermediates themselves is simple and high yield, only using the most commonly-used 7-methoxy-tetralone as original starting material and undergoing one step of reaction to obtain the intermediates, followed by one more step of converting the intermediate compounds to desired product agomelatine. Said reaction processes are greatly simplified, with the reaction yield being improved and the difficulty in purification of previous method being overcome, as compare with the previous technique for preparation of agomelatine. Typically, the yield of the present invention is over 70%.

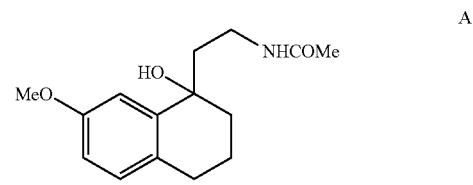

A

16 Claims, No Drawings

AGOMELATINE INTERMEDIATES AND PREPARATION METHOD THEREOF

FIELD OF THE INVENTION

The invention relates to intermediate compounds for preparation of agomelatine, as well as the preparation methods thereof.

BACKGROUND OF THE INVENTION

Agomelatine has a chemical structure as shown in Formula (I), with the chemical name N-[2-(7-methoxy-1-naphthyl)ethyl]acetamide and trade name Valdoxan. It has dual pharmacological effects, which is not only the agonist of melatonergic system receptors, but also the antagonist of $5HT_{2C}$ receptor. Said properties confer activity in the central nervous system, especially in the treatment of major depression, seasonal affective disorders, dyssomnia, cardiovascular diseases, digestive system diseases, insomnia and fatigue caused by jet lag, appetite disorders and obesity. It is the first melatonin type antidepressive agent, which can effectively treat depressive disorders, improve the sleep parameters and maintain sexual function. It was approved by EU on Feb. 24, 2009, with the trade name Valdoxan®/Thymanax®.

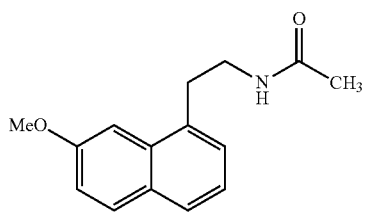

Taking into account the compound's pharmaceutical value, it is important to obtain the compound in an effective industrial synthetic method, which can be easily converted into large-scale production in the industry and obtain agomelatine in good yield and high purity.

Many synthetic methods for agomelatine have been reported, which can be roughly divided into four types, in which all of the starting materials are the compound of formula (II). European patent specification EP0447285 reported a method for preparation of agomelatine (I): reacting 7-methoxy-tetralone (II) with ethyl bromoacetate by Reformatsky reaction, and then dehydro-aromatization with sulfur to obtain (7-methoxy-1-naphthyl)acetic acid ethyl ester (IV), followed by hydrolysis, acyl chlorination, ammonification, dehydration and reduction to yield the compound (VIII), which is finally acetylated to obtain agomelatine (I), as shown below:

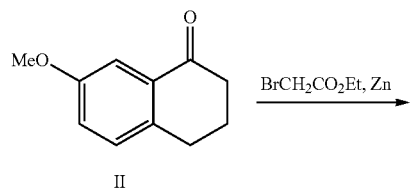

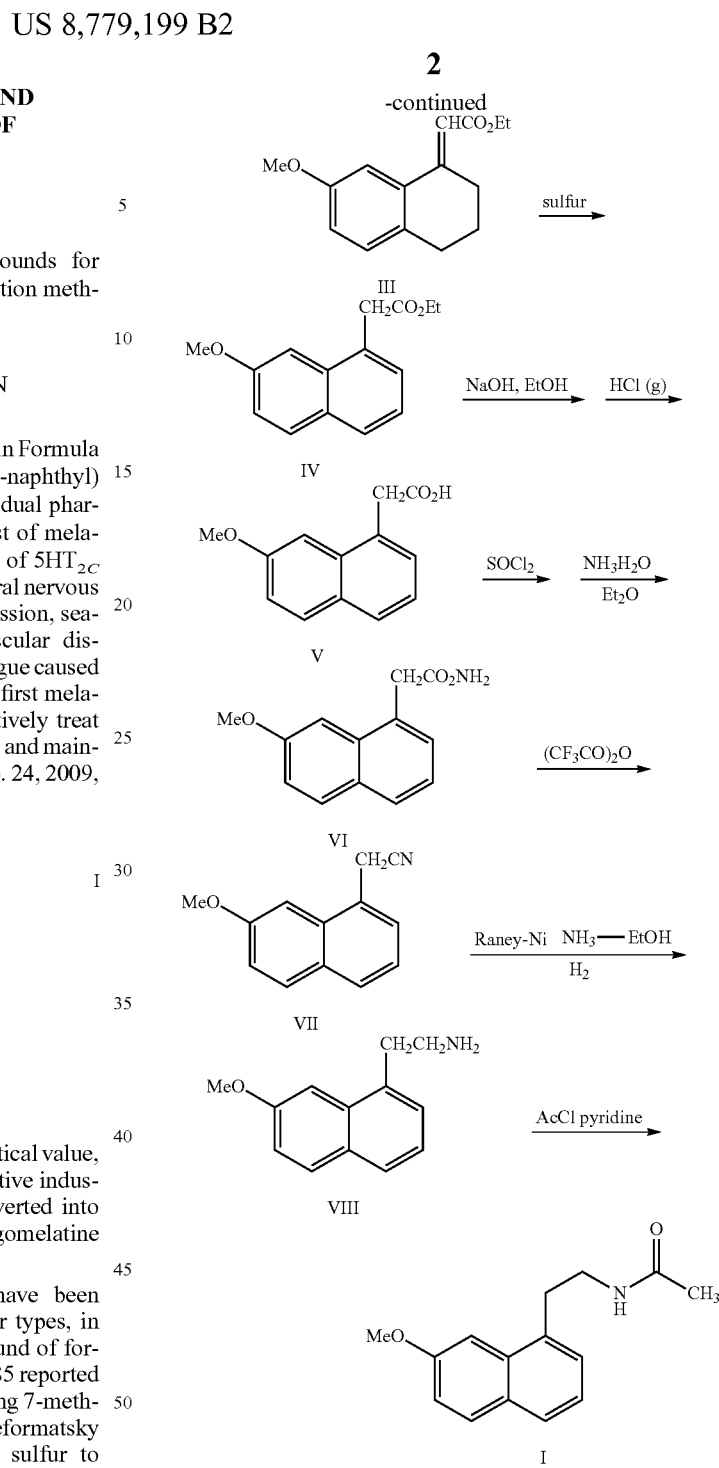

However, there are some defects in the above method, which comprise:
(1) it takes eight steps to synthesize 2-(7-methoxy-1-naphthyl)ethylamine, thereby rendering the average yield being less than 30%;
(2) when the above method is converted into industrial scale, it is difficult to carry out the reaction, mainly due to the poor reproducibility of the first step; the first step comprises reacting 7-methoxy-tetralone (II) with ethyl bromoacetate by Reformatsky reaction to produce ethyl (7-methoxy-3,4-dihydronaphthalen-1(2H)-ylidene)acetate, which requires benzene as the solvent; considering the environmental factors, said step does not meet the requirements of large-scale production; and (3) the next step for aromatization of ethyl (7-methoxy-3,4-dihydronaphthalen-1(2H)-ylidene)acetate is usually incomplete, and after saponification often results in a mixture, from which it is difficult to separate pure product (IV).

Chinese patent specification CN1680284 reported another method for agomelatine synthesis: reaction of 7-methoxy-tetralone (II) with cyano-acetic acid produces intermediate compound (IX), the intermediate (IX) is dehydrogenated in the presence of hydrogenation catalyst Pd-C, with allyl methacrylate as the dehydrogenating agent, followed by reduction to generate compound (VIII), and finally the compound (VIII) is converted to agomelatine (I) by acetylation. The total yield is about 72%, as shown below:

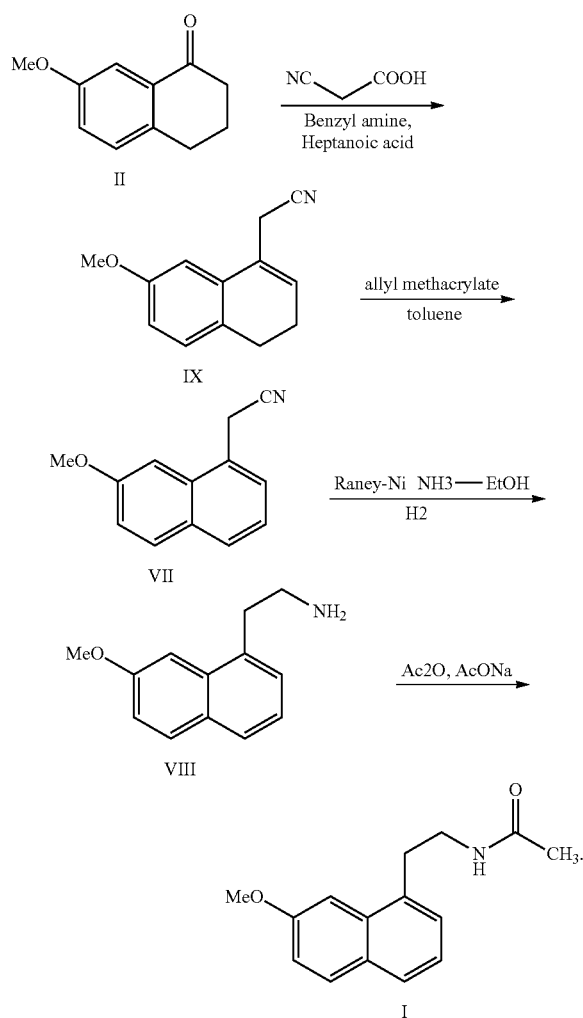

But there are some defects in the above method:
(1) some carcinogenic agents are used in the reaction route, for example, benzylamine/heptanoic acid catalyst system with great toxicity is used in the conversion of formula (II) to formula (IX);
(2) propyl methacrylate is used as the dehydrogenating agent during the conversion of formula (IX) to (VII), which results in a lot of environmental pollution, moreover, this step of reaction actually was found to be low yield and difficult to reproduce; and
(3) during the hydrogenation process of conversion of formula (VII) to (VIII), a by-product having formula (XII) generated; since the nature of the by-product is similar to the desired product and this step is the penultimate step, it is difficult to purify the desired product and the yield loss after recrystallization is large.

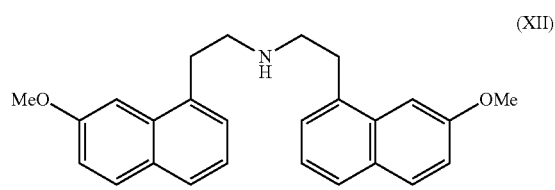 [SMILES: COc1ccc2cccc(CCNCCc3cccc4ccc(OC)cc34)c2c1]

Considering the medicinal value and good market prospects of agomelatine, it is important to synthesize the compound of formula (I) in an effective manner for industrialization.

DISCLOSURE OF THE INVENTION

One objective of the present invention is to provide two novel intermediate compounds for preparation of agomelatine. When we use these new compounds to prepare agomelatine, it is simple to manipulate and easy for working-up (without complicated operations such as rectification and column chromatography separation), well-controlled, with high purity and yield, and suitable for industrial production.

Another objective of the present invention is to provide preparation methods for the two intermediate compounds above and the use thereof.

For these purposes, the following technical solutions are used in the present invention.

The compound of formula (A) is used:

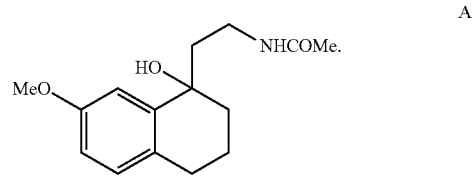

The method for preparation of the compound of formula (A) is reductive acylation of the compound of formula (C) under the condition of catalytic hydrogenation, in the presence of acetic anhydride.

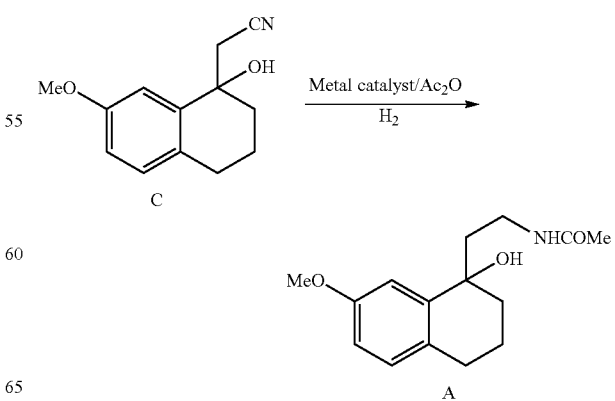

The catalyst used in the conversion of the compound of formula (C) to the compound of formula (A) is conventional metal catalyst, such as activated cobalt, activated nickel (Ni), preferably Raney-Ni; the amount of catalyst can be 0.1-0.3 times the amount of the compound C by weight; the amount of acetic anhydride is 1-3 times the molar amount of the compound C, more preferably 1-1.3 times. The organic solvent used in this reaction is commonly-used organic solvents, such as dioxane, THF, acetonitrile or acetic anhydride, preferably THF. The optimal reaction temperature is 10-50° C., more preferably 20-30° C. The reaction time depends on the complete consumption of reactants detected, typically is 6-12 hours. After the reaction is completed, the working-up procedure can be performed according to conventional methods in the art.

The method for preparation of agomelatine using the compound A is provided in the present invention, comprising dehydration and aromatization of the compound A to obtain the desired product of formula I:

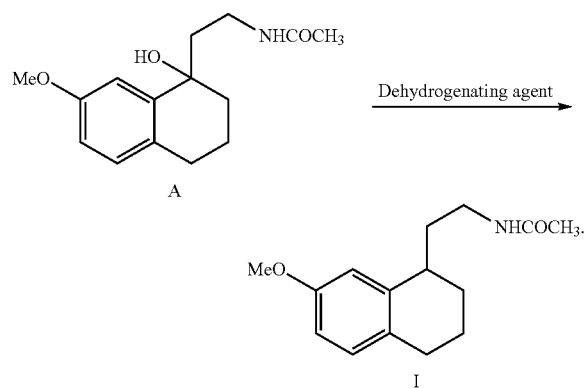

In the conversion of the compound A to the compound I by aromatization as shown above, the dehydrogenating agent is preferably dichloro-dicyanobenzoquinone (DDQ), the amount of said dehydrogenating agent is preferably 1-3 times the molar amount of the compound A, more preferably 1-1.3 times. The organic solvent used in this reaction is commonly-used organic solvents, eg. one of toluene, dioxane, THF, acetonitrile or glacial acetic acid, or any mixture thereof, preferably the mixture of toluene and glacial acetic acid, the mixture of acetonitrile and glacial acetic acid, or glacial acetic acid. The amount of said organic solvent is generally 10-50 ml/g of the compound A. The reaction temperature is preferably 30-150° C., more preferably 50-100° C. The reaction time depends on the complete consumption of reactants detected, typically is from 30 minutes to 12 hours. After the reaction is completed, the working-up procedure can be performed according to conventional methods in the art.

The compound of formula (B) is used:

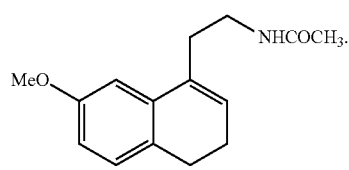

The method for preparation of the compound of formula (B) is dehydration of the compound A under acidic condition:

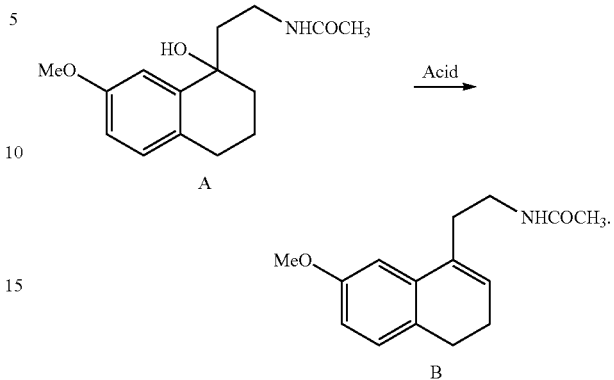

The acid used in the conversion of the compound A to the compound B is a conventional acid, such as hydrohalogen acid, sulfuric acid, acetic acid, and the like. The organic solvent used is commonly-used organic solvent, such as alcohols, dioxane, THF, or acetonitrile, preferably alcohol solvent, eg., ethyl acetate, acetone and the like. The amount of said organic solvent is generally 10-50 ml/g of the compound A. The reaction temperature is preferably −20-40° C., more preferably 0-30° C. The reaction time depends on the complete consumption of reactants detected, typically is 1-3 hours. After the reaction is completed, the working-up procedure can be performed according to conventional methods in the art.

The method for preparation of agomelatine using the compound B is provided in the present invention, comprising reaction of the compound B with a dehydrogenating agent, to obtain the desired product of formula I:

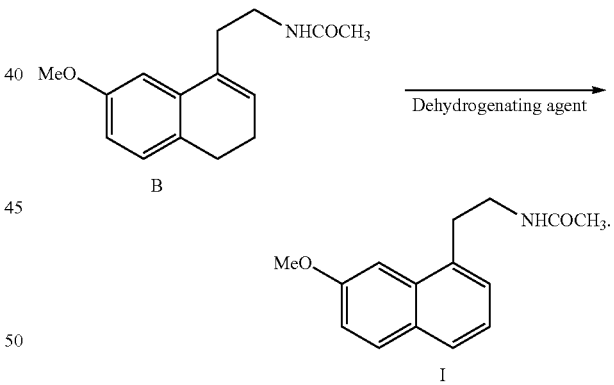

In the conversion of the compound B to the compound I, the dehydrogenating agent is preferably dichloro-dicyanobenzoquinone (DDQ), the amount of said dehydrogenating agent is preferably 1-3 times the molar amount of the compound B, more preferably 1-1.3 times. The organic solvent used in this reaction is commonly-used organic solvents, such as dichloromethane, dioxane, THF, acetonitrile, glacial acetic acid, or the like, preferably dichloromethane or toluene. The amount of said organic solvent is generally 10-50 ml/g of the compound B. The reaction temperature is preferably 0-50° C., more preferably 10-30° C. The reaction time depends on the complete consumption of reactants detected, typically is from 30 minutes to 6 hours. After the reaction is completed, the working-up procedure can be performed according to conventional methods in the art.

The method for preparation of agomelatine comprises the following steps:

a. reductive acylation of the compound C under the condition of catalytic hydrogenation and in the presence of acetic anhydride to obtain compound A

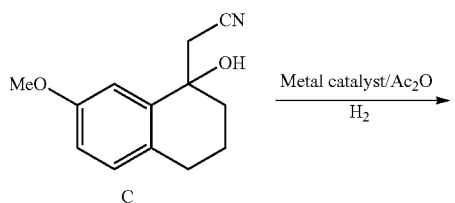

b. dehydration and aromatization of the compound A with a dehydrogenating agent, to obtain the desired product of formula I

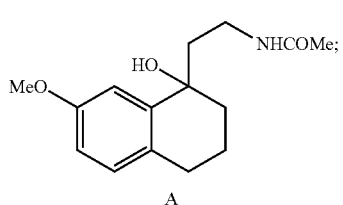

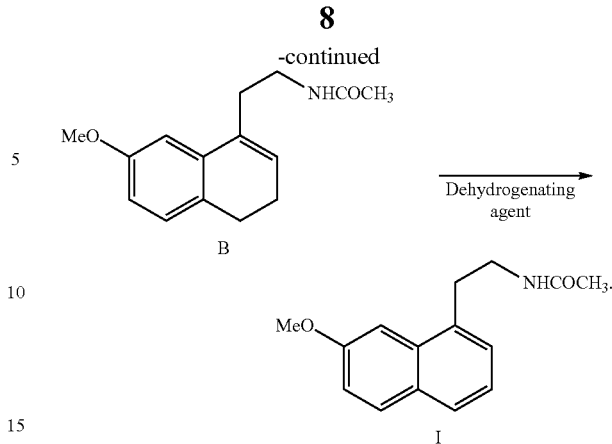

The intermediate compound of formula C can be made by the condensation of formula II and acetonitrile in the presence of catalyst

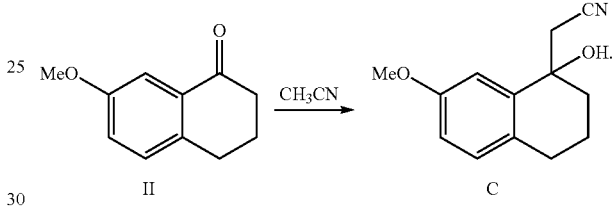

The catalyst used in the conversion of the compound of formula II to the compound of formula (C) is butyl lithium. Both the amount of catalyst and the amount of acetonitrile are 1-3 times the molar amount of the compound II, more preferably 1-1.3 times. The organic solvent used in this reaction is anhydrous organic solvent, such as dioxane, THF, and the like, which needs dehydration treatment or can be purchased directly from commercial suppliers. The amount of said organic solvent usually is 5-20 ml/g of the compound II. The optimal reaction temperature is from −80 to −50° C., more preferably from −70 to −60° C. The reaction time depends on the complete consumption of reactants detected, typically is from 1 minute to 3 hours. After the reaction is completed, the working-up procedure can be performed according to conventional methods in the art.

The compound C can also be prepared according to the methods disclosed in related literatures such as *Journal of Medicinal Chemistry*, 1976, 19(6), 803.

The reagents and starting materials used in the present invention are commercially available, unless specified otherwise.

The advantages of the present invention are:

the invention provides two novel intermediate compounds; when we use these new compounds to prepare agomelatine, it is simple to manipulate and easy for working-up, without complicated operations such as rectification and column chromatography separation, well-controlled, with high purity, and suitable for industrial production. Meanwhile, the preparation method of the two new intermediates themselves is simple and high yield, only using the most commonly-used 7-methoxy-tetralone (II) as original starting material and undergoing one step of reaction to obtain the intermediates, followed by one more step of converting the intermediate compounds to desired product agomelatine. Said reaction processes are greatly simplified, with the reaction yield being improved and the difficulty in purification of previous method In the method for preparation of agomelatine in the present invention, we can also use the following route, comprising firstly dehydrating compound A under acidic condition to produce compound B, then reacting compound B with a dehydrogenating agent to obtain the desired product of formula I

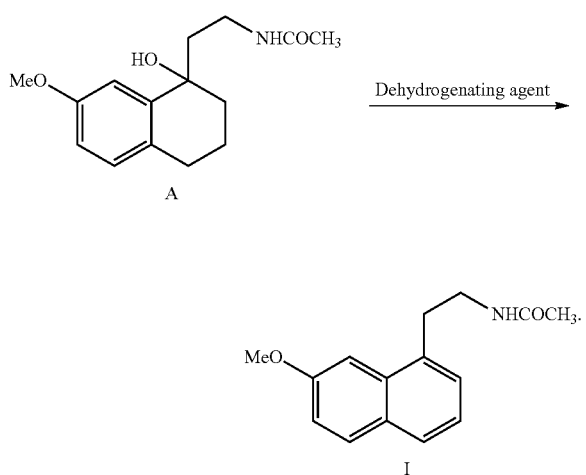

being overcome, as compare with the previous technique for preparation of agomelatine. Typically, the yield of the present invention is over 70%.

EXAMPLES

The following examples are utilized for further illustration of the present invention, but they are not intended to limit the scope of the invention in any manner.

Example 1

1) Synthesis of 2-(1-hydroxyl-7-methoxy-1,2,3,4-tetrahydro-naphthalen-1-yl)-acetonitrile (the Compound C)

To a reaction vessel was added acetonitrile (19.0 ml) and anhydrous THF (50 ml), cooled to −70° C. with dry ice/ethanol, then the solution of n-Butyl Lithium in n-hexane (2.5 M, 142.0 ml) was added dropwise slowly. After stirring for half an hour under this temperature, the solution of the compound II (44.6 g) in anhydrous THF (300 ml) was added dropwise slowly, and stirred for 1 h at the same temperature. The reaction is quenched by adding saturated aqueous ammonium chloride (700 ml), extracted with ethyl acetate (350 ml×3). The organic layers were combined, washed with saturated aqueous NaCl (350 ml), dried over anhydrous sodium sulfate, and concentrated to obtain the off-white title product (54.3 g). Yield: 98.3%.

Example 2

2) Synthesis of N-[2-(1-hydroxyl-7-methoxy-1,2,3,4-tetrahydro-naphthalen-1-yl)ethyl]-acetamide (the Compound A)

The compound C (54.3 g) was dissolved in THF (500 ml), and acetic anhydride (33.1 g) and Raney-Ni (10 g) were then added. The reaction mixture was hydrogenated with the hydrogen pressure maintaining 1.1 Mpa at temperature 30° C., until the reaction is completed. The mixture was cooled to room temperature, filtered and concentrated to remove THF. The residue was diluted with ethyl acetate (500 ml), washed with saturated aqueous $NaHCO_3$ (150 ml), water (150 ml) and saturated aqueous NaCl (150 ml). The resulting organic phase was dried over anhydrous sodium sulfate, filtered and concentrated to obtain the off-white product A (56.0 g). Yield: 85%

$^1$HNMR ($CDCl_3$) δ: 1.77-1.98 (m, 4H), 1.92 (s, 3H), 2.01-2.11(m, 2H), 2.28(s, OH), 2.67-2.77 (m, 2H), 3.28-3.50 (m, 2H), 3.80 (s, 3H), 6.32 (s, NH), 6.74-7.27 (m, 3H).

ESI-MS (m/z): 286.1 (M+Na).

Mp: 106-109° C.

Example 3

3) Synthesis of N-[2-(7-methoxy-1-naphthyl)ethyl]acetamide (the compound I)

The compound A (56.0 g) was dissolved in toluene (500 ml) and acetic acid (50 ml), DDQ (53.2 g) was added, and the mixture was heated at 40° C. for about 5 h. After the reaction was completed, the mixture was filtered, and the filtrate was washed with saturated aqueous $NaHCO_3$ (250 ml×2), water (250 ml) and saturated aqueous NaCl (250 ml). The resulting organic phase was dried over anhydrous sodium sulfate, filtered and the solvent was evaporated off. The residue was recrystallized from ethanol-water (1:1), dried in an oven to obtain the title product as white powder (43.8 g). Yield: 85%.

$^1$HNMR($CDCl_3$) δ: 1.922 (s, 3H), 3.21-3.24(t, 2H), 3.56-3.61(q, 2H), 3.96(s, 3H), 5.97 (s, 1H), 7.14-7.16 (q, 1H), 7.22-7.26 (m, 2H), 7.46-7.47 (m, 1H), 7.64-7.67 (m, 1H), 7.72-7.74 (d, 1H). ESI -MS(m/z): 244.14 (M+H).

Example 4

1) Synthesis of 2-(1-hydroxyl-7-methoxy-1,2,3,4-tetrahydro-naphthalen-1-yl)-acetonitrile (the Compound C)

To a reaction vessel was added acetonitrile (9.5 ml) and anhydrous THF (25 ml), cooled to −70° C. with dry ice/ethanol, and then the solution of n-Butyl Lithium in n-hexane (2.5 M, 71.0 ml) was added dropwise slowly. After stirring for half an hour under this temperature, the solution of the compound II (22.3 g) in anhydrous THF (150 ml) was added dropwise slowly, and stirred for 1 h at the same temperature. The reaction is quenched by adding saturated aqueous ammonium chloride (350 ml), extracted with ethyl acetate (200 ml×3). The organic layers were combined, washed with saturated aqueous NaCl (200 ml), dried over anhydrous sodium sulfate, and concentrated to obtain the off-white title product (27.2 g) e. Yield: 98.4%.

Example 5

2) Synthesis of N-[2-(1-hydroxyl-7-methoxy-1,2,3,4-tetrahydro-naphthalen-1-yl)ethyl]-acetamide (the Compound A)

The compound C (27.2 g) was dissolved in THF (250 ml), and acetic anhydride (15.6 g) and Raney-Ni (4 g) were then added. The reaction mixture was hydrogenated with the hydrogen pressure maintaining 1.1 Mpa at temperature 30° C., until the reaction is completed. The mixture was cooled to room temperature, filtered and concentrated to remove THF. The residue was diluted with ethyl acetate (250 ml), washed with saturated aqueous $NaHCO_3$ (100 ml), water (100 ml) and saturated aqueous NaCl (100 ml). The resulting organic phase was dried over anhydrous sodium sulfate, filtered and concentrated to obtain the off-white title product (28.0 g). Yield: 85%.

$^1$HNMR ($CDCl_3$) δ: 1.77-1.98 (m, 4H), 1.92 (s, 3H), 2.01-2.11 (m, 2H), 2.28 (s, OH), 2.67-2.77 (m, 2H), 3.28-3.50 (m, 2H), 3.80 (s, 3H), 6.32 (s, NH), 6.74-7.27 (m, 3H).

ESI-MS (m/z): 286.1 (M+Na).

Mp: 106-109° C.

Example 6

3) Synthesis of N-[2-(7-methoxy-3,4-dihydro-naphthalen-1-yl)ethyl]acetamide (the Compound B)

The compound A (28.0 g) was dissolved in ethyl acetate (300 ml) to form a suspension, to which concentrated HCl (12 M, 13.3 ml) was then added dropwise at RT. The suspension gradually turned clear. The reaction solution was further stirred for 2 h and poured into water (150 ml). After the layers separated, the organic phase was washed with saturated aqueous $NaHCO_3$ (150 ml×2) and saturated aqueous NaCl (150 ml), dried over anhydrous sodium sulfate, filtered and concentrated to obtain the title product as oil (25.5 g). Yield: 97.8%.

¹HNMR (CDCl₃) δ: 1.944 (s, 3H), 2.21-2.27 (m, 2H), 2.61-2.69 (m, 4H), 3.40-3.45 (m, 2H), 3.80 (s, 3H), 5.59 (s, NH), 5.90-5.93 (m, 1H), 6.68-7.05 (m, 3H).
ESI –MS (m/z): 268.3 (M+Na).

Example 7

4) Synthesis of N-[2-(7-methoxy-1-naphthyl)ethyl]acetamide (the compound I)

The compound B (25.5 g) was dissolved in dichloromethane (250 ml), DDQ (26.1 g) was added portionwise, and the mixture was stirred overnight at RT. After the reaction was completed, the mixture was filtered, and the filtrate was washed with saturated aqueous NaHCO₃ (150 ml×2), water (150 ml) and saturated aqueous NaCl (150 ml). The organic phase obtained was dried over anhydrous sodium sulfate, filtered and the solvent was evaporated off. The residue was recrystallized from ethanol-water (1:1), dried in an oven to obtain white powder (46.4 g). Yield: 91.8%.

¹HNMR(CDCl₃) δ: 1.922 (s, 3H), 3.21-3.24(t, 2H), 3.56-3.61(q, 2H), 3.96(s, 3H), 5.97 (s, 1H), 7.14-7.16 (q, 1H), 7.22-7.26 (m, 2H), 7.46-7.47 (m, 1H), 7.64-7.67 (m, 1H), 7.72-7.74 (d, 1H). ESI -MS(m/z): 244.14 (M+H).

The invention claimed is:

1. A compound A of the following formula

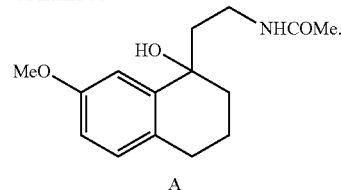

A

2. A compound B of following formula:

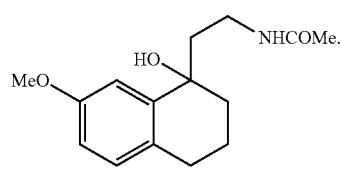

B

3. A method for the preparation of the compound A. of claim 1, comprising reductive acylation of compound C under catalytic hydrogenation conditions in the presence of acetic anhydride

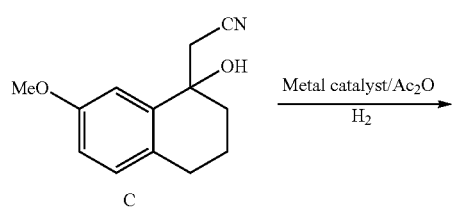

4. The method according to claim 3, wherein the metal catalyst is Raney-Ni, the amount of which is 0.1-0.3 times the amount of the compound C by weight.

5. The method according to claim 3, wherein the amount of the acetic anhydride is 1-1.3 times the molar amount of the compound C.

6. A method for preparation of agomelatine using the compound A, comprising dehydration and aromatization of the compound A to obtain agomelatine of formula I:

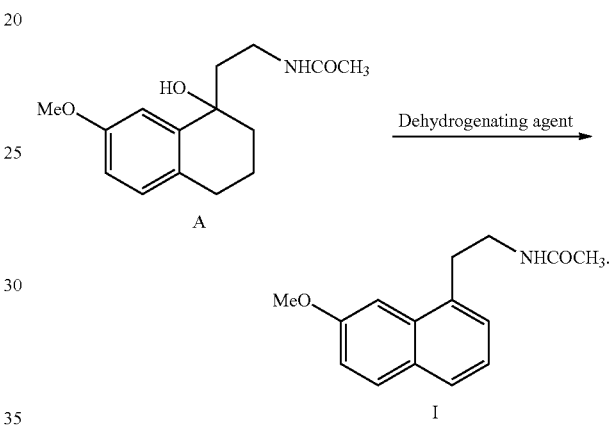

7. The method according to claim 6, wherein the dehydrogenating agent used in the aromatization is dichloro-dicyanobenzoquinone.

8. The method according to claim 6, wherein the amount of dehydrogenating agent is 1-3 times the molar amount of the compound A.

9. The method according to claim 6, wherein the solvent used in the reaction is a mixture of toluene and glacial acetic acid, a mixture of acetonitrile and glacial acetic acid, or glacial acetic acid.

10. A method for the preparation of the compound B of Claim 2, comprising dehydration of the compound A under acidic conditions:

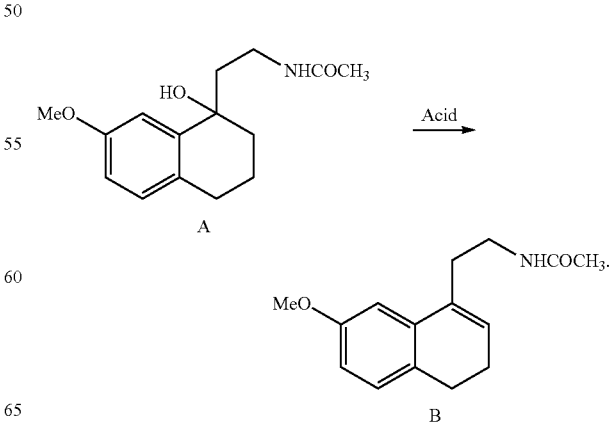

11. A method for preparation of agomelatine using the compound B, comprising reaction of the compound B with a dehydrogenating agent to obtain agomelatine of formula I:

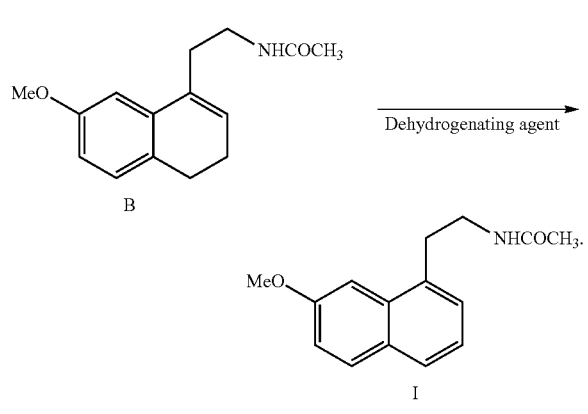

12. The method according to claim 11, wherein the dehydrogenating agent is dichloro-dicyanobenzoquinone.

13. The method according to claim 11, wherein the amount of the dehydrogenating agent is 1-3 times the molar amount of the compound B.

14. The method according to claim 11, wherein the organic solvent used in the reaction is dichloromethane or toluene.

15. A method for preparation of agomelatine, comprising the following steps:
   a. reductive acylation of compound C under catalytic hydrogenation conditions in the presence of acetic anhydride to obtain compound A

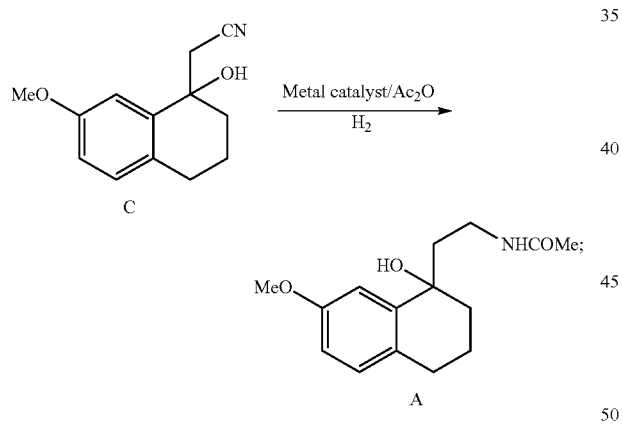

b. dehydration and aromatization of the compound A with a dehydrogenating agent, to obtain agomelatine of formula I

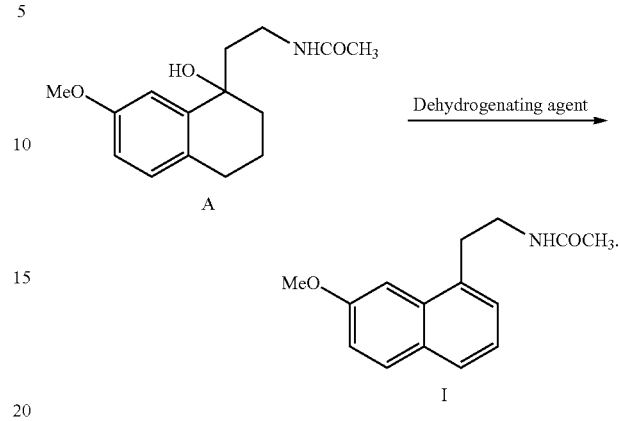

16. The method according to claim 15, wherein compound A is dehydrated under acidic conditions to produce the compound B, which compound B is then reacted with a dehydrogenating agent to obtain agomelatine of formula I

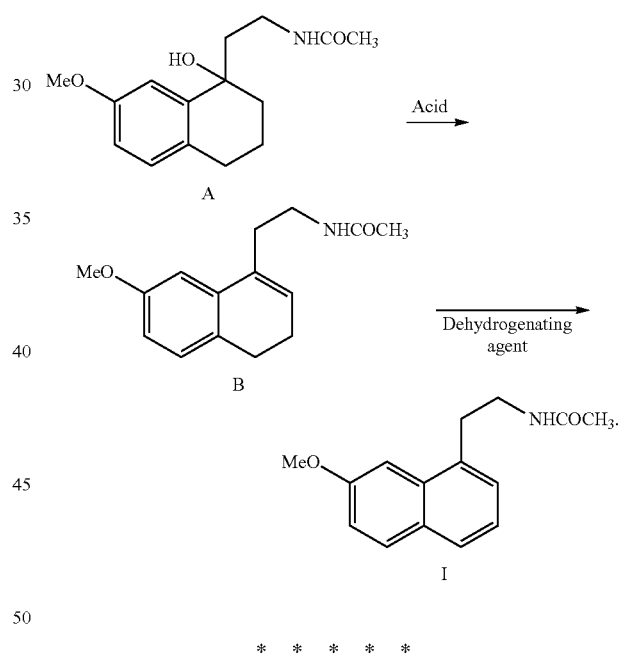

* * * * *

UNITED STATES PATENT AND TRADEMARK OFFICE
CERTIFICATE OF CORRECTION

| | | |
|---|---|---|
| PATENT NO. | : 8,779,199 B2 | Page 1 of 1 |
| APPLICATION NO. | : 13/702388 | |
| DATED | : July 15, 2014 | |
| INVENTOR(S) | : Peng Zhang et al. | |

It is certified that error appears in the above-identified patent and that said Letters Patent is hereby corrected as shown below:

Title Page, References Cited, line 2: "2005/0182258" should be --2008/0182268--

Signed and Sealed this
Fourth Day of November, 2014

Michelle K. Lee
*Deputy Director of the United States Patent and Trademark Office*